US009237753B2

(12) United States Patent
Giuliani et al.

(10) Patent No.: US 9,237,753 B2
(45) Date of Patent: Jan. 19, 2016

(54) MIXTURE OF LACTIC BACTERIA FOR THE PREPARATION OF GLUTEN FREE BAKED PRODUCTS

(75) Inventors: Giammaria Giuliani, Milan (IT); Anna Benedusi, Bari (IT); Raffaella Di Cagno, Bari (IT); Maria De Angelis, Bari (IT); Antonella Luisi, Bari (IT); Marco Gobbetti, Bari (IT)

(73) Assignee: GIULIANI S.P.A., Milan (IL)

( * ) Notice: Subject to any disclaimer, the term of this patent is extended or adjusted under 35 U.S.C. 154(b) by 1669 days.

(21) Appl. No.: 12/374,246

(22) PCT Filed: Jul. 3, 2007

(86) PCT No.: PCT/IT2007/000479
§ 371 (c)(1),
(2), (4) Date: Nov. 6, 2009

(87) PCT Pub. No.: WO2008/010252
PCT Pub. Date: Jan. 24, 2008

(65) Prior Publication Data
US 2010/0055238 A1    Mar. 4, 2010

(30) Foreign Application Priority Data

Jul. 17, 2006  (IT) .............................. RM2006A0369

(51) Int. Cl.
| | |
|---|---|
| *C12N 1/20* | (2006.01) |
| *A21D 8/04* | (2006.01) |
| *A21D 13/04* | (2006.01) |
| *A21D 13/06* | (2006.01) |
| *C12R 1/01* | (2006.01) |
| *C12R 1/225* | (2006.01) |
| *C12R 1/24* | (2006.01) |
| *C12R 1/25* | (2006.01) |
| *A21D 10/00* | (2006.01) |

(52) U.S. Cl.
CPC *A21D 8/04* (2013.01); *A21D 8/045* (2013.01); *A21D 10/002* (2013.01); *A21D 13/04* (2013.01); *A21D 13/066* (2013.01); *C12N 1/20* (2013.01); *C12R 1/01* (2013.01); *C12R 1/225* (2013.01); *C12R 1/24* (2013.01); *C12R 1/25* (2013.01); *A23Y 2220/05* (2013.01); *A23Y 2220/13* (2013.01); *A23Y 2220/17* (2013.01); *A23Y 2220/25* (2013.01); *A23Y 2220/29* (2013.01); *A23Y 2220/35* (2013.01); *A23Y 2220/37* (2013.01); *A23Y 2220/39* (2013.01); *A23Y 2220/63* (2013.01); *A23Y 2220/65* (2013.01); *A23Y 2220/67* (2013.01); *A23Y 2220/81* (2013.01)

(58) Field of Classification Search
None
See application file for complete search history.

(56) References Cited

U.S. PATENT DOCUMENTS 5,108,766 A * 4/1992 Gelinas et al. .................. 426/43
6,159,724 A   12/2000 Ehret

FOREIGN PATENT DOCUMENTS

DE         297 04 037 U1    5/1997

OTHER PUBLICATIONS

Paramithiotis et al. (Process Biochemistry 40 (2005) 2813-2819).*
Gerez et al. ("Gluten breakdown by *lactobacilli* and *pediococci* strains isolated from sourdough", Letters in Applied Microbiology, vol. 42, No. 5, May 2006, pp. 459-464).*
deAngelis et al. ("Fermentation by selected sourdough lactic acid bacteria to decrease coeliac intolerance to rye flour" Journal of Cereal Science, vol. 43, No. 3, May 2006, pp. 301-314).*
Aslam et al. (International Journal of Systematic and Evolutionary Microbiology (2006), 56, 2209-2213 ).*
Corsetti et al.( International Journal of Systematic and Evolutionary Microbiology (2005), 55, 35-40).*
Raffaella Di Cagno et al., "Sourdough Bread Made from Wheat and Nontoxic Flours and Started with Selected Lactobacilli Is Tolerated in Celiac Sprue Patients," Applied and Environmental Microbiology, No. 70, No. 2, pp. 10881096, Feb. 2004, 9 pages.
International Search Report dated Apr. 7, 2008 issued in International Patent Application No. PCT/IT2007/000479, 5 pages.

* cited by examiner

*Primary Examiner* — Irene Marx
(74) *Attorney, Agent, or Firm* — Arent Fox LLP

(57) ABSTRACT

The present invention concerns a mixture of lactic bacteria for yeasting of gluten-free baked products. Particularly, the invention concerns the use of "natural yeast" based on selected lactic bacteria as yeasting agent for the production of gluten-free bread, with improved sensory and nutritional property, designed for celiac patients feeding.

10 Claims, 8 Drawing Sheets

*Lactobacillus sanfranciscensis* (DSM18426) (SEQ ID NO:3)
```
  1 agtccccatt gattcttagt gcttgcanta agatgatttt ggatccgact gagtggcgaa
 61 ctggtgagta acacgtgggt aacctgccca gaagaagggg ataacacctg gaaacagatg
121 ctaataccgt ataacaacaa gaaccacatg gttcttgttt gaaagctggc ctttgtgcta
181 gtgcttctgg atggacccgc ggcgtattag ctagttggtg agataatagc tcaccaaggc
241 aatgatacgt agcagacctg agagggtaat ctgccacaat gggactgaga cacgcccat
301 actcctacgg gaggcagcag tagggaatct tccacaatgg acgaaagtct gatggagcaa
361 cgccgcgtga gtgaagaagg gtttcggctc gtaaaactct gttgttagag aagaacagcc
421 gtgagagcaa ctgctcacgg tatgacggta tctaaccaga aagtcacggc taactacgtg
481 ccagcagccg cggtaatacg taggtggcaa acgttgtccg gatttattgg gcgtaaaggg
541 agcgcaggcg gtttattaag tctgatgtga agccttcgg cttaacccga aaagtgcatc
601 ggaaactgat aaacttgagt gcanaaaagg atantggaac ttcatgtgta ncngtgaaaa
661 tgcgtaaata tttnaangaa caccagtggc gaaggcngnt atctggtctg taactgnaa
```

*Lactobacillus sanfranciscensis* (DSM 18427) (SEQ ID NO:4)
```
  1 gacgantccc cattgattct tagtgcttgc antaagatga ttttggatcc gactgagtgg
 61 cgaactggtg agtaacacgt gggtaacctg cccagaagaa ggggataaca cctggaaaca
121 gatgctaata ccgtataaca acaagaacca catggttctt gtttgaaagc tggcctttgt
181 gctagtgctt ctggatggac ccgcggcgta ttagctagtt ggtgagataa tagctcacca
241 aggcaatgat acgtagcaga cctgagaggg taatctgcca caatgggact gagacacggc
301 ccatactcct acgggaggca gcagtaggga atcttccaca atggacgaaa gtctgatgga
361 gcaacgccgc gtgagtgaag aagggtttcg gctcgtaaaa ctctgttgtt agagaagaac
421 agccgtgaga gcaactgctc acggtatgac ggtatctaac cagaaagtca cggctaacta
481 cgtgccagca gccgcggtaa tacgtaggtg gcaaacgttg tccggatttta ttgggcgtaa
541 agggagcgc angcggttta ttaantctga tgtgaaagcc ttcgcttaac ccganaantg
601 catcgaaact gataaacttg aatgcaaaaa ggggggggg ggggnnntgt gtaccgttaa
661 attcctaaat atttnaaagg aacaccantg gcgaaggcgg ctatntggtc tntaaaaaaa
721 aaacacnccc cctnnntncg ggg
```

*Lactobacillus plantarum* (DSM18430) (SEQ ID NO:5)
```
TTTCTTCCCAATGGACGAAAGTCTGATGGAGCAACGCCGCGTGAGTGAAGAAGGGTTTCGGCTCGTAAAA
CTCTGTTGTTAAAGAAGAACATATCTGAGAGTAACTGTTCAGGTATTGACGGTATTTAACCAGAAAGCCA
CGGCTAACTACGTGCCAGCAGCCGCGGTAATACGTAGGTGGCAAGCGTTGTCCGGATTTATTGGGCGTAA
AGCGAGCGCAGGCGGTTTTTTAAGTCTGATGTGAAAGCCTTCGGCTCAACCGAAGAAGTGCATCGGAAAC
TGGGAAACTTGAGTGCAGAAGAGGACAGTGGAACTCCATGTGTAGCGGTGAAATGCGTAGATATATGGA
AGAACACCAGTGGCGAAGGCGGCTGTCTGGTCTGTAACTGACGCTGAGGCTCGAAAGTATGGGTAGCAA
ACAGGATTAGATACCCTGGTAGTCCATACCGTAAACGATGAATGCTAAGTGTTGGAGGGTTTCCGCCCTT
CAGTGCTGCAGCTAACGCATTAAGCATTCCGCCTGGGGAGTACGGCCGCAAGGCTGAAACTCAAAGGAA
TTGACGGGGGCCCGCACAAGCGGTGGAGCATGTGGTTTAATTCGAAGCTACGCGAAGAACCTTACCAGGT
CTTGACATACTATGCAAATCTAAGAGATTAGACGTTCCCTTTCGGGGACATGGATACAGGTGGTGCATGG
TTGTCGTCAGCTCGTGTCGTGAGATGTTGGGTTAAGTCCCGCAACGAGCGCA
```

Fig. 1

● bread control
● fermented bread

MIXTURE OF LACTIC BACTERIA FOR THE PREPARATION OF GLUTEN FREE BAKED PRODUCTS

CROSS-REFERENCE TO RELATED APPLICATION

This application is a National Stage entry of International Application No. PCT/IT2007/000479, filed Jul. 3, 2007, which claims priority to Italian Application number RM2006A000369 filed Jul. 17, 2006, the disclosure of the prior applications are hereby incorporated in their entirety by reference.

The present invention concerns a mixture of lactic bacteria for the preparation of gluten free baked products. Particularly, the invention concerns the use of "natural yeast" based on lactic bacteria selected as "yeasting agent" for the production of gluten-free bread to be used by celiac patients. The use of selected lactic bacteria and proposed production protocol allow an improvement of organoleptic nutritional and storageability characteristics in comparison to gluten-free obtained bread using brewer's yeast or chemical yeasting.

The epidemiology of gluten intolerance or celiac disease is continuously growing. Last surveys with reference to the European and United States population report an incidence of 1/100 individual (Revers, 2005. Epidemiology of celiac disease: what are the prevalence, incidence, and progression of celiac disease? *Gastroenterology.* 128:47-51). According to current knowledge the only effective therapeutic remedy against this food intolerance is a diet completely lacking in gluten (gluten-free) to be rigorously maintained for all the life (Hamer, 2005. Celiac Disease: Background and biochemical aspects. *Biotechnol Advanc* 23:401-408). Celiac patients subjected to a stringent dietetic regimen (zero tolerance) recover, in many cases, the normal morphology of the villas and intestinal crypts (Hamer, 2005. Celiac Disease: Background and biochemical aspects. *Biotechnol Advanc* 23:401-408).

As reported in Standard Codex adopted by the World Health Organisation (WHO) and Food and Agricultural Organisation (FAO) are defined gluten-free foods according to following: (i) are prepared from originally not containing wheat ingredients (all species of genus *Triticum*), spelt, kamut, rye, barley, oat or their crossed varieties and with gluten concentration lower than 20 ppm; (ii) are prepared using ingredients extracted from wheat, spelt, rye, barley, oat or their crossed varieties and are made gluten-free with a gluten concentration not higher than 200 ppm; and (iii) are prepared from a mixture of item (i) and (ii) ingredients with a gluten concentration not higher than 200 ppm. A large variety of gluten-free products is commercially available: bread, pizza, biscuit and pasta (Gallagher et al 2004. Recent advances in the formulation of gluten-free cereal-based products. *Trends Food Ski Technol* 15:143-152). Generally the quality of gluten-free bread, in terms of sensory and rheological characteristics, is lower than the bread prepared from wheat flour or rye (Gallagher et al., 2004. Recent advances in the formulation of gluten-free cereal-based products. *Trends Food Ski Technol* 15:143-152). The absence of gluten and, therefore, difficultly replaceable structural properties, and the application of production protocols adapted for non conventional ingredients, mainly determine lower quality (Gallagher et al., 2004. Recent advances in the formulation of gluten-free cereal-based products. *Trends Food Ski Technol* 15:143-152). The most recent literature reports show various studies carried out in order to improve the rheological and storageability properties. In particular, the use of differently occurring starches, (Gallagher et al., 2002. Novel rices starches in gluten-free bread. *Proceedings of the International Association of Cereal Chemists Conference.* 24-26; Demiate et al., 2000. Relationship between baking behaviour of modified cassava starches and starch chemical structure by FTIR spectroscopy. *Carbohyd Polym* 42:149-158), rubbers and other hydrocolloids is reported (for example hydroxy propyl methyl cellulose, carrageenans, xanthanes) (Kang et al., 1997. *Kor Jour Food Ski Technol* 29:700-704; Schwarzlaff et al., 1996. Guar and locust bean gums as partial replacers of all-purpose flour in bread: an objective and sensory evaluation. *J Food Qual* 19:217-229), soy proteins (Ranhorta et al., 1975. Preparation and fortification of soy-fortified gluten-free bread. *J Food Sci* 40:62-64) and milk powders and rice (Gallagher et al., 2003. The effect of dairy and powder addition on loaf and crumb characteristics, and on shelf life (intermediate and long-term) of gluten-free breads stored in a modified atmosphere. *Eur Food Res Technol* 218:44-48), which in various formulations can contribute to improve the structure and shelf-life of the gluten-free products. Since it has been demonstrated that the celiac patients are subjected to a lower absorption of fibres, minerals and other nutrients, in comparison to individuals subjected to a normal alimentary regimen (Grehn et al., 2001. Dietary habits of Swedish adult celiac patients treated by to gluten-free diet for 10 years. *Scand J Nutr* 45:178-182; Mariani et al., 1998. The gluten-free diet: a nutritional risk factor for adolescents with celiac disease. *J Pediatr Gastroenterol Nut* 27:519-523), the enrichment of gluten-free products with fibres of various origins (for example inuline) has been also considered by various research groups (Gibson and Roberfroid, 1995. Dietary modulation of the human colonic microbiota: introducing the concept of prebiotics. *J Nut* 125:1401-1412; Taylor and Parker, 2002. Quinoa. *Pseudocereals and less common cereals, wheat properties and utilisation potential* 93-122; Tosi et al., 1996. Utilisation of whole *amaranthus (Amarantus cruentus)* flour in the manufacture of biscuits for celiacs. *Alimentaria* 34:49-51). The technology of gluten-free products is mainly based on the use of yeasting chemicals or brewer's yeast (*Saccharomyces cerevisiae*) (Gallagher et al., 2004. Recent advances in the formulation of gluten-free cereal-based products. *Trends Food Ski Technol* 15:143-152). According to current knowledge it is known the Patent Application WO02065842 concerning a starter for the production of bread and baked products, in particular gluten-free, wherein said starter is based on *Lactobacillus fermentum*. Further a study is known (Arendt unpublished data in Katina et al., 2005. Potential of sourdough for healthier cereal products. *Trends Food Sci Technol* 16:104-112) wherein is described the use of "natural yeast" as biological and natural yeasting agent for the gluten-free bread production, based on rice, soy, saracen wheat and xanthanes, in order to boost the taste and aroma, and extend the shelf-life. Obtained results have demonstrated that the use of "natural yeast" is technologically possible also in gluten-free products and in particular the storageability and taste are improved in comparison to same products obtained using brewer's yeast or chemical yeasting. The "natural yeast", a cocktail of lactic bacteria and yeasts originated from raw matter, is frequently used in the technology of yeasted baked products. Various studies carried out in last decade (Gobbetti et al., 2005. Bacteria Biochemistry and physiology of sourdough lactic acid bacteria. *Trends Food Sci Technol* 16:57-69) demonstrated that the acidification process and peptidase activity exerted by the lactic bacteria of natural yeast are suitable to improve taste, rheological, nutritional and storageability characteristics of baked yeasted products. Recent studies (Di Cagno et al., 2002. Proteolysis by sourdough lactic acid bacteria: Effects on wheat flour protein fractions and gliadin peptides involved in human cereal intolerance. *Appl Environ Microbiol* 68:623-633; Di Cagno et al., 2004. A sourdough bread made from wheat and non-toxic flours and started with selected lactobacilli is tolerated in celiac sprue. *Appl Environ Microbiol* 70:1088-1096; De Angelis et al., 2005. VSL#3 probiotic preparation has the capacity to hydrolyse gliadin polypeptides responsible for celiac sprue. *Biochim Biophys Acta-Moleculare Basis of Disease* 1762:80-93) demonstrated that lactic bacteria of "natural yeast", when selected for their proteolytic activity, are able to degrade remarkably gluten fractions responsible for celiac pathology. In this context, some studies (Størsrud et al., 2003. Gluten contamination in oat products and products naturally free from gluten. *Eur Food Res Technol* 217:281-485) carried out on commercially available products in North-Europe demonstrated that remarkable percentage (about 30%) of gluten-free products can be contaminated by gluten traces (100-300 ppm), which can constitute possible risk for the individuals subjected to this intolerance.

Based on the literature reported and above described data, some problems appear to be prior with reference to quality of the gluten-free products: (i) to improve sensory quality since too much different from conventional products; (ii) to increase the nutritional value in order to abridge the absorption deficiency of celiac patients; (iii) to reduce the contaminating risks from gluten possibly occurring in field or during the transformation process; and (iv) to extend the storageability.

In the light of above it is therefore apparent the need to provide materials and methods for the preparation of baked products not displaying disadvantages of known ones.

The Authors of the present invention have now discovered a "natural yeast" consisting of a mixture of selected lactic-.bacteria and provided a production protocol suitable to enhance the taste and nutritional characteristics, which can be considered technological instruments suitable to solve the priority problems for the quality of gluten-free bread. Lactic bacteria according to the present invention belong to the *Lactobacillus* genus and have been previously isolated from "natural yeast" for the production of Centre and Southern Italy typical bread. The selection has been carried out among 55 breads isolated based on proteolytic, acidifying, phytase activities and more generally on the ability to determine optimal sensory characteristics.

Lactic bacteria according to the present invention, have been deposited on 11 Jul. 2006 at DSMZ qualified collection centre, which assigned for every bacterium the following deposit numbers according to following correspondence:
*Lactobacillus sanfranciscensis* LS40=DSM 18426
*L. sanfranciscensis* LS41=DSM 18427
*Lactobacillus rossiae* LR15=DSM 18428
*Lactobacillus rossiae* Ci35=DSM 18429
*Lactobacillus plantarum* CF1=DSM 18430
*Lactobacillus curvatus* 1Hd=DSM 18431
*Lactobacillus farciminis* 2XA3=DSM 18432

However, after the shipment to DSMZ it has been communicated to the agency that really the correct denominations of *Lactobacillus curvatus* 1Hd and *Lactobacillus farciminis* 2XA3 are *Lactobacillus brevis* 1Hd and *Pediococcus pentosaceus* 2XA3.

Therefore, in the continuation of the disclosure, the bacteria according to the invention *Lactobacillus sanfranciscensis* LS40, *L. sanfranciscensis* LS41, *Lactobacillus rossiae* LR15, *Lactobacillus rossiae* Ci35, *Lactobacillus plantarum* CF1, *Lactobacillus brevis* 1Hd, *Pediococcus pentosaceus* 2XA3 from now on will be denominated respectively *Lactobacillus sanfranciscensis* (DSM 18426), *L. sanfranciscensis* (DSM 18427), *Lactobacillus rossiae* (DSM 18428), *Lactobacillus rossiae* (DSM 18429), *Lactobacillus plantarum* (DSM 18430), *Lactobacillus brevis* (DSM 18431), *Pediococcus pentosaceus* (DSM 18432).

Particularly, the following mixture to be used in the form of "natural yeast" has been selected: *Lactobacillus sanfranciscensis* (DSM 18426), *L. sanfranciscensis* (DSM 18427) and *Lactobacillus plantarum* (DSM 18430). FIG. 1 shows the partial sequences of 16S rRNA genes of *L. sanfranciscensis* (DSM 18426), *L. sanfranciscensis* (DSM 18427) and *L. plantarum* (DSM 18430) obtained by PCR amplification using LpigF/LiPR primer. (TACGGGAGGCAGCAGTAG/CATG-GTGTGACGGGCGGT, respectively SEQ ID NO: 1 and SEQ ID NO: 2).

A propagation protocol of "natural yeast" involving propagation thereof for 8-24 h in a knead consisting of gluten-free ingredients and its successive use has been standardized and optimized, at various percentages according to desired characteristics, like natural starter or ingredient for a short yeasting (about 1-3 h) preceding the bread baking.

The fermentation process using "natural yeast" according to the present invention allows (i) a possible gluten detoxification (about 300 ppm) of the gluten occurring as a contaminant in the gluten-free ingredients; (ii) increases by 3-10 times, depending on dosage and using type, the concentration of free amino acids in comparison to the use of brewer's yeast as yeasting agent, thus improving the nutritional value of bread; (iii) is characterised by a phytase activity by about 10 times higher than using brewer's yeast as yeasting agent, increasing therefore the bioavailability of bread mineral salts as demonstrated with reference to $Ca^{2+}$ and $Zn^{2+}$ using atomic absorption spectrophotometry; (iv) allows the sensory properties to be improved, in comparison to the use of brewer's yeast as yeasting agent, conferring a traditional bread typical taste and aroma; and (v) determines a better shelf-life of the bread avoiding the use of chemical conservative agents. Moreover, the strain mixture according to the present invention displays peptidase type activity and acidification power much higher than obtained with *L. fermentum* used in prior art. Enzymatic activities of the mixture according to the present invention have the nutritional advantage of favouring higher release of amino acids thus increasing nutritional availabilities thereof; freeing a greater amount of precursors of volatile compounds generated during the baking process and responsible of bread typical aroma; and contributing to the detoxification of possible gluten traces, as gluten-free product contaminant.

Lactic bacteria *Lactobacillus rossiae* (DSM 18429) and (DSM 18428), *Lactobacillus brevis* (DSM 18431) and *Pediococcus pentosaceus* (DSM 18432) can be used in various formulations differing in comparison to the above mixture mainly from the sensory point of view.

It is therefore a specific object of the present invention a mixture of lactic bacteria strains for the yeasting of gluten-free flours comprising or consisting of at least two, preferably at least three lactic bacteria strains selected from the group consisting of *Lactobacillus sanfranciscensis* (DSM 18426), *Lactobacillus rossiae* (DSM 18429), *Lactobacillus plantarum* (DSM 18430), *L. sanfranciscensis* (DSM 18427), *Pediococcus pentosaceus* (DSM 18432), *L. rossiae* (DSM 18428) and *Lactobacillus brevis* (DSM 18431).

According to preferred embodiments the following mixtures, at equal ratio among the species or strains, comprising or consisting of *Lactobacillus sanfranciscensis* (DSM 18426), *Lactobacillus rossiae* (DSM 18429) and *Lactobacillus plantarum* (DSM 18430); *L. sanfranciscensis* (DSM 18426), *L. sanfranciscensis* (DSM 18427) and *L. plantarum* (DSM 18430); *Pediococcus pentosaceus* (DSM 18432), *L.* rossiae (DSM 18428) and *L. plantarum* (DSM 18430); *Lactobacillus brevis* (DSM 18431), *L. rossiae* (DSM 18429) and *L. plantarum* (DSM 18430); or *L. sanfranciscensis* (DSM 18426), *L. sanfranciscensis* (DSM 18427) and *L. rossiae* (DSM 18429) can be used.

The microorganism mixture according to the present invention can be used for yeasting of gluten-free flours as, for example, flours from corn, rice, saracen wheat, tapioca starch, sunflower, linen, teff, sorgho, quinoa, potato, manioca, amaranth and millet.

A gluten-free flour composition to be used in the two fermentation processes for the preparation of a starter for gluten-free baked products or the same gluten-free baked products using the strain mixture as above defined constitutes a further object of the present invention, said flour composition comprising or consisting of corn starch 10-30%, preferably 12%, tapioca starch 2-10%, preferably 4%, rice flour 20-60%, preferably 32% and saracen wheat flour 1-10%, preferably 6%, wherein said percentages are expressed as % weight of flour composition total weight. To the mixtures to be used for to the preparation of gluten-free baked products are added other ingredients, as guar gum, xanthanes, glycerin, inuline, sorbitol, soy protein hydrolysate, soy lecithin, olive oil, sunflower oil, sugar, salt, milk serum and skim milk powder used at various percentages (0.5-3.0%) depending on product type.

A further object of the present invention refers to a process for the preparation of a yeast starter (also called "natural yeast" according to the present invention in the experimental section) for gluten-free baked products comprising the following steps:
a) culture propagation of the lactic bacteria strain mixture as above defined;
b) mixing of the flour composition as above defined at 50-65% concentration with 35-50% water, containing the bacteria strain mixture as defined in step a) having a cell density of about $10^8$ ufc/g;
c) fermentation for 8-24 hours at 20-30° C.

Further the process can comprise a d) drying or freezing step of the starter obtained in step c).

Further the present invention concerns a process for the preparation of gluten-free baked products comprising the following steps:
a) knead the flour composition as above defined in percentage of 40-60%, preferably 44%, water 10-30%, preferably 26%, containing brewer's yeast 1-3% and salt 0.1-1.2%, and fresh starter inoculum, obtainable according to the above describe process, in amount from 5 to 30%, preferably 30% (when the percentage is lower than 30%, amounts of flour and water are proportionally increased), or dried, like ingredient without yeasting activity, or frozen with yeasting activity, said percentages being weight percentages with reference to the total weight of the knead;
b) allow the fermentation for approximately 1-3 hours at 30° C.;
c) cook for 50 minutes at 220° C.

It is a further object of the present invention a starter mixture obtainable using the above defined process. Moreover, the present invention concerns baked products obtainable using the above defined process, as, for example, bread.

The present invention now will be described by way of illustration and not limitation, according to preferred embodiments thereof, with particular reference to the enclosed drawings wherein:

FIG. 1 shows the partial sequences of 16S rRNA genes of *Lactobacillus sanfranciscensis* (DSM 18426), *L. sanfranciscensis* (DSM 18427) and *Lactobacillus plantarum* (DSM 18430) (SEQ ID NO: 3, SEQ ID NO: 4, SEQ ID NO: 5, respectively);

FIG. 2 shows N type amino peptidase activity (a), proline iminopeptidase (b), dipeptidase (c), tripeptidase (d), prolidase (e) and prolinase (f) of strains belonging to *Lactobacillus sanfranciscensis*, species respectively on Leu-p-NA, For-p-NA, Leu-Leu, Leu-Leu-Leu, Val-Pro and For-Gly synthetic substrates. The enzymatic activity has been expressed as activity unit (u), that is the enzyme amount necessary in order to release 1 μmol/min p-nitroanilide or 1 μmol/min amino acid for di- and tri-peptidase activities.

Example 1

Figure 2:
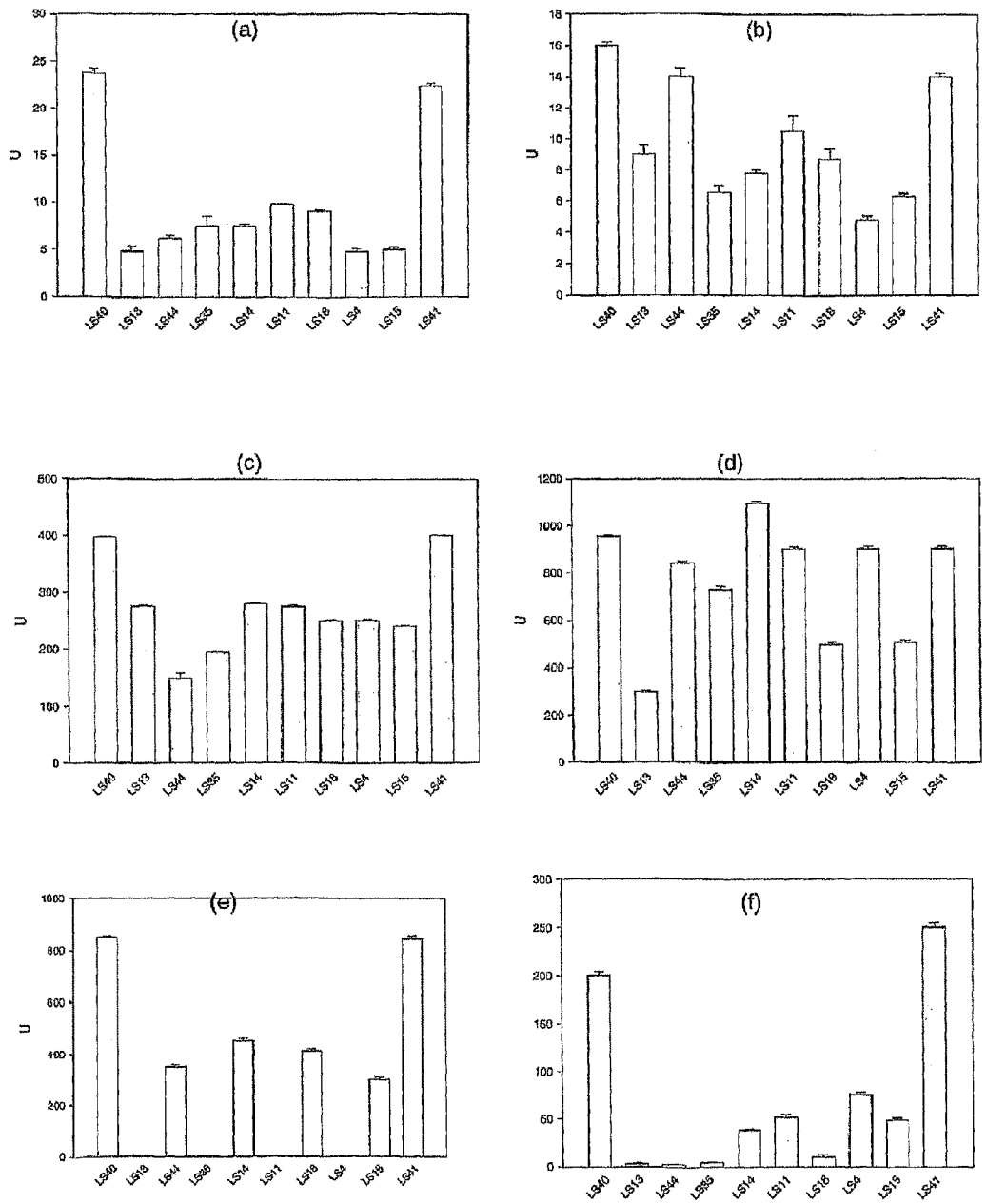

Selection and Analysis of Strains According to the Present Invention

Fifty five strains of lactic bacteria belonging to the Collezione di Colture del Dipartimento di Protezione delle Piante e Microbiologia Applicata dell'Università degli Studi di Bari, previously isolated from "natural yeasts", have been propagated at 30° C. for 24 h in modified MRS (mMRS), containing, in addition to the normal ingredients, 6% maltose and 10% of yeast water—final pH 5.6. In Table 1 the list of lactic bacteria species isolated from "natural yeast" and used in the present invention.

TABLE 1

| Species | Strains |
|---|---|
| *Lactobacillus sanfransiscensis* | (DSM 18426), LS13, LS44, LS35, LS14, LS11, LS18, LS4, LS15, (DSM 18427) |

TABLE 1-continued

| Species | Strains |
|---|---|
| Lactobacillus rossiae | (DSM 18429), (DSM 18428), LR19, LR13, LR22, LR24, LR25, LR8, LR18, LR20 |
| Lactobacillus plantarum | DC400, (DSM 18430), DB200, 20196, 2MF8, 3DM, G10C3 |
| Lactobacillus brevis | (DSM 18431), 5Z, CR13, AM7, 1D, 2Hb |
| Lactobacillus pentosus | 8CF, 12H5, 12H6, 14H9 |
| Lactobacillus alimentarius | 2B |
| Lactobacillus fermentum | 2S1, D13 |
| Lactobacillus casei subsp. casei | 2752, 2756, 2766 |
| Lactobacillus paracasei | 12H8, 12H1, 1Hb, 4H3 |
| Lactobacillus curvatus | 14H10, 13H5 |
| Pediococcus pentosaceus | (DSM 18432) |
| Lactobacillus helveticus | B26W |
| Lactobacillus delbrueckii | B15Z |
| Lactobacillus gasseri | B24W, B30W |
| Lactobacillus amylovorus | L. amylovorus |

Preferred lactic bacteria according to the invention L. sanfranciscensis (DSM 18426), L. sanfranciscensis (DSM 18427) and L. plantarum (DSM 18430) have been characterised by sequencing, as illustrated in FIG. 1.

(1) Proteolytic Activity

The selection based on proteolytic activity has been carried out using cells cultured for 24 h, harvested by centrifugation (10,000 g×10 min, 4° C.), washed twice in phosphate buffer 50 mM, pH 7.0 and re-suspended in the same buffer at 2.5 optical density ($A_{620nm}$), correspondent to a cellular density of 108 ufc/ml. Proteinase activity has been tested on albumins and globulins extracted from wheat flour (Weiss, et al., 1993. Electrophoretic characterisation of wheat grain allergens from different cultivars involved in baker's asthma, *Electrophoresis* 14:805-816). The reaction mixture, containing 0.9 ml of the albumin-globulin fraction (ca. 4 mg/ml of protein) and 0.1 ml of cell suspension, has been incubated at 30° C. for 48 h under stirring (150 rpm). SDS-PAGE mono-dimensional electrophoresis has been carried out according to Laemmli system (Laemmli, 1970. Cleavage of structural proteins during the assembly of the head of bacteriophage T4, *Nature* 227:680-685). Type N aminopeptidase (PepN) and proline iminopeptidase (PepI) activities, have been determined using synthetic substrates, respectively, Leu-p-NA and For-p-NA. The reaction mixture comprised: 0.9 ml of K-phosphate buffer 50 mM, pH 7.0 wherein synthetic substrate was dissolved (final concentration 2 mM) and 100µλ of cell suspension. Enzymatic activity, expressed as activity unit (U), correspond to the enzyme amount necessary to release 1 µmol/min p-nitroanilide (Gobbetti et al., 1996. The proteolytic system of *Lactobacillus sanfranciscensis* CB1: purification and characterisation of a proteinase, dipeptidase, and aminopeptidase. *Appl. Environ. Microbiol.* 62:3220-3226). Prolidase (PepQ) and prolinase (PepR) have been determined as described by Di Cagno and coworkers, (Di Cagno et al., 2004. Sourdough bread made from wheat and nontoxic flours and starter with selected lactobacilli is tolerated in celiac sprue patients, *Appl. Environ. Microbiol.* 70:1088-1096) on, respectively, Val-Pro and For-Gly. Dipeptidase (PepV) and tripeptidase (PepT) have been determined according to Cd-ninidrine method (Gobbetti et al., 1999. Study of the effects of temperature, pH, NaCl, and aw on the proteolytic and lipolytic activities of cheese-related lactic acid bacteria by quadratic response surface methodology, *Enzyme Microbial Technol* 25:795-809) using, respectively, Leu-Leu and Leu-Leu-Leu. An activity unit (U) has been defined as the enzyme amount necessary in order to release 1 µmol of amino acid/min.

(2) Acidification Power

The selection based on the acidification power has been carried out on 100 g of knead (knead yield 160) using 62.51 g of flour mixture, as native corn, white corn, rice flour and saracen wheat flour, at 15, 15, 65 and 5 weight %, and 37.5 ml of water containing cell suspension of the single lactic bacteria at final cell density $10^8$ ufc/g of knead. Acidification kinetics of the kneads has been detected on-line measuring pH (pH-meter 507, Crison, Italy). The data have been modelled using Gompertz equation modified by Zwietering and co-workers (Zwietering et al., 1990. Modelling of bacterial growth curve. *Appl Environ Microbiol* 56: 1875-1881).

(3) Gluten Detoxification

Gluten detoxification tests have been carried out on 100 g of knead (knead yield 160) using 62.51 g of flour mixture, as native corn, white corn, rice flour and saracen wheat flour, at 15, 15, 65 and 5%, and 37.5 ml of water containing the cell suspensions of the selected lactic bacteria for the higher proteolytic activity (*Lactobacillus sanfranciscensis* (DSM 18426), (DSM 18427), *Lactobacillus rossiae* (DSM 18429), (DSM 18428), *Pediococcus pentosaceus* (DSM 18432) and *Lactobacillus brevis* (DSM 18431)) at a final cell density $10^8$ ufc/g of knead. A gluten amount of 500 or 1000 ppm has been added to knead. Two control kneads containing, respectively, 500 and 1000 ppm of gluten, and 0.15 g of $NaN_3$ (p/p), have been produced without bacterial inoculum and chemically acidified at pH 3.6. The kneads have been incubated at 30° C. for 5, 24 and 48 h. At the end of the fermentation, ELISA test was used for the gluten quantification (Transia Plate, Diffchamb).

(4) Characterisation of the Fermented Kneads

Selected lactic bacteria have been used in five different formulations employed for the production of kneads based on a flour mixture consisting of native corn, white corn, rice flour and saracen wheat flour (Table 2).

TABLE 2

| "Natural yeast" Formulations | Species |
|---|---|
| 1 | Lactobacillus sanfranciscensis (DSM 18426) |
|  | Lactobacillus rossiae (DSM 18429) |
|  | Lactobacillus plantarum (DSM 18430) |
| 2 | L. sanfranciscensis (DSM 18426) |
|  | L. sanfranciscensis (DSM 18427) |
|  | L. plantarum (DSM 18430) |
| 3 | Pediococcus pentosaceus (DSM 18432) |
|  | L. rossiae (DSM 18428) |
|  | L. s plantarum (DSM 18430) |
| 4 | Lactobacillus brevis (DSM 18431) |
|  | L. rossiae (DSM 18429) |
|  | L. plantarum (DSM 18430) |
| 5 | L. sanfranciscensis (DSM 18426) |
|  | L. sanfranciscensis (DSM 18427) |
|  | L. rossiae (DSM 18429) |

The produced kneads as previously indicated have been incubated for 24 h at 30° C. A knead without bacterial inoculum, fermented using brewer's yeast (1.5%) for 2 h at 30° C., was used as control. The characterisation of the kneads fermented with the different formulations and correspondent control included: (i) acidification kinetics (Zwietering et al., 1990. Modelling of bacterial growth curves. *Appl Environ Microbiol* 56: 1875-1881); (ii) the determination of organic acids (D- and L-lactic acid and acetic acid) produced during the fermentation by means of enzymatic kits (DHFF CHAMB Italy Srl, Italy) (iii) cell density by plate counting on mMRS agar (Oxoid, Basingstoke, Hampshire, England), (iv) phytase activity by detection of released inorganic orthophosphate, using the method described by Fiske and Subbarow (Fiske and Subbarow, 1925. The colorimetric determination of phosphorus. *J. Biol. Chem.* 66:375) and Shimizu (Shimizu, 1992. Purification and characterisation of phytase from *Bacillus subtilis* (Natto) n-77. *Biosci. Biotechnol. Biochem.* 56:1266-1269); and (v) the determination of total amino acid content by means of "Amino Acid Analyser Biochrom 30" (Biochrom Ltd, Cambridge, UK), using a cationic exchange column (Na Oxidised Feedstuff, 20 cm×4.6 mm).

(5) Production of Gluten-free Bread

The different formulations of selected "natural yeast" have been used for the production of gluten-free bread considering various technological solutions. After fermentation for 24 h, it has been used as (i) fresh natural starter by inoculating at 5-30% base knead consisting of above reported ingredients or like (ii) ingredient (15%) providing the preliminary drying. Brewer's yeast (1%) and NaCl (0.3%) were added to the kneads and incubated at 30° C. for 2 h before the baking (50 min at 220° C.) in laboratory oven. A control bread control was produced using knead fermented with brewer's yeast (2%) at 30° C. for 2 h. The following determinations were carried out on produced breads: (i) analysis of the bioavailable mineral element content by water extraction and subsequent determination by atomic absorption spectrophotometry; (ii) sensory analysis by panel test carried out by 6 not trained tasters (Haglund et al., 1998. Sensory evaluation of wholemeal bread from ecologically and conventionally grown wheat. *J. Cereal Sci.* 27:199-207) and using for each attribute a continuous scale of increasing intensity in the value range from 0 to 100; (iii) analysis of the specific volume and hardness according to AACC 10-10 and AACC 74-09 official methods (Approved Association Cereal Chemistry, X Edition, Ed. AACC, St. Paul, Minn.—U.S.A.); and (iv) shelf-life test by means of bread production on industrial scale, packaging in modified atmosphere (40% $N_2$ and 60% $CO_2$) and successive storage for 6 months in absence of conservative chemical compounds.

Results (1) Proteinase Activity

Proteinase activity, determined using albumins and globulins as substrate, evidenced heterogeneous hydrolysis profiles. In FIG. 2 results relating to strains belonging to *L. sanfranciscensis* species are reported. It is possible to observe that for all considered enzymatic activities, with the exception of tripeptidase type activity, strains (DSM 18426) and (DSM 18427) have activity remarkably higher than other strains: According to the same criterion the selection for strains belonging to other species was carried out. The availability of a Culture Collection for the screening and the large number of assayed enzymatic activities constitute the premise in order to obtain not generally available selected strains. *L. sanfranciscensis* (DSM 18426) and (DSM 18427), *L. rossiae* (DSM 18429) and (DSM 18428), *L. brevis* (DSM 18431) and *P. pentosaceus* (DSM 18432) were selected on the base of proteinase and peptidase activities. In particular, a comparison of peptidase type activities of selected species and strains with two *Lactobacillu fermentum* strains used in initial screening always pointed out higher peptidase activity (40-80% on average) for all tested substrates. Enzymatic activities based on which the selection has been carried out can have a multiple value: (i) to favour a greater release of amino acids thus increasing nutritional availabilities; (ii) to release greater amount of volatile compound precursors generated during the baking process and responsible for the typical bread aroma; and (iii) to contribute to the detoxification of possible gluten traces, as contaminant of the gluten-free products.

(2) Acidification Power

Figure 3:
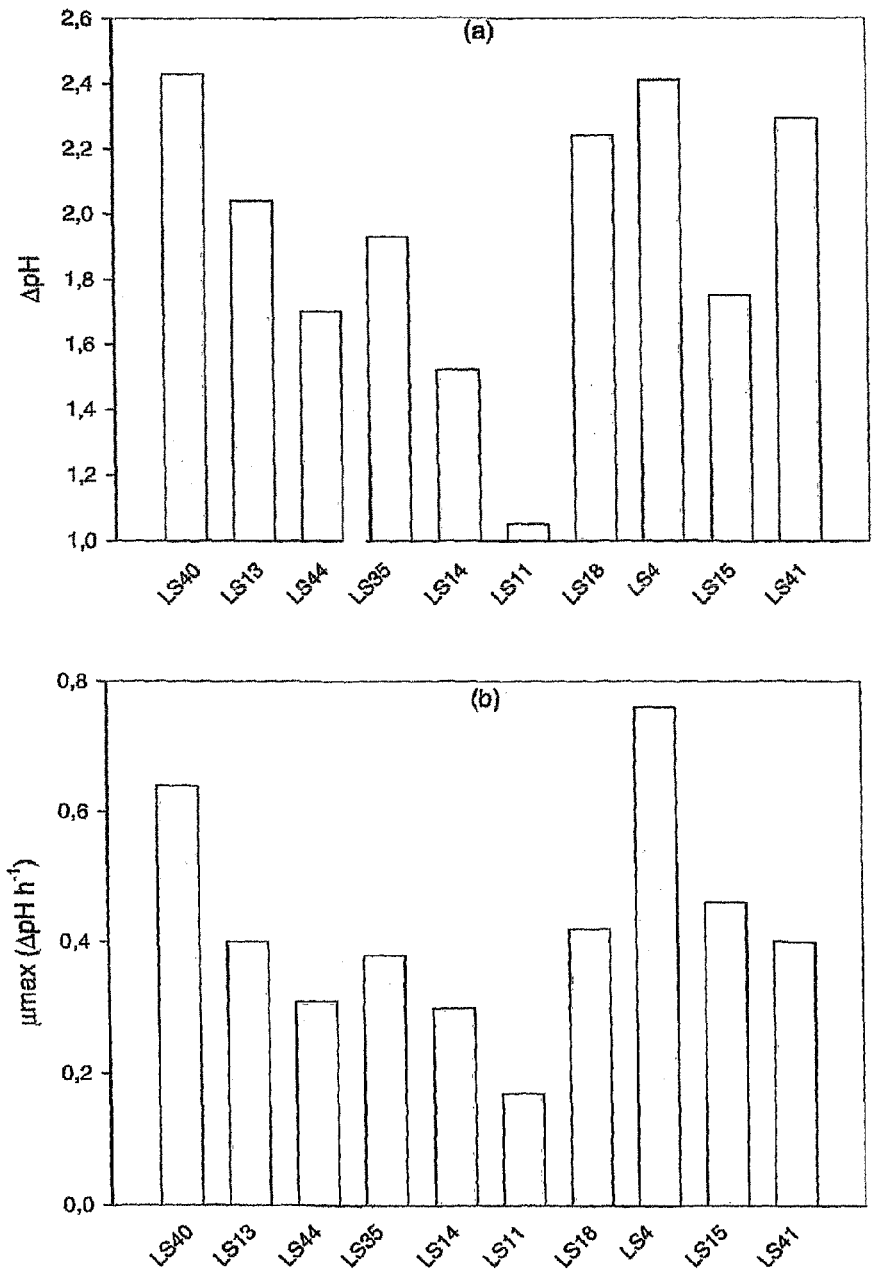
FIG. 3 shows ΔpH (difference between initial and final pH values) (a) and $\mu_{max}$ (highest speed of acidification) (b) of kneads fermented for 7 h at 30° C. with strains belonging to *Lactobacillus sanfranciscensis* species.

The acidification power of lactic bacteria isolates has been directly determined on acid kneads fermented with single microorganism for 7 h at 30° C. In FIG. 3 results relating to strains belonging to *L. sanfranciscensis* species are reported. It is possible to observe that (DSM 18426) strains, and in particular (DSM 18427), have been characterised also by a good acidification power, expressed in terms of ΔpH and μmax. The selection for strains belonging to other species was carried out according to the same criterion. In particular, *L. plantarum* (DSM 18430) has been selected on the base of acidification power characterised by ΔpH values higher than 2.3. All selected species or strains displayed acidification power and velocity higher than those determined for two *L. fermentum* strains considered in the screening.

(3) Gluten Detoxification

Lactic bacteria pool selected based on proteolysis activity (*L. sanfranciscensis* (18426) and (DSM 18427), *L. rossiae* (DSM 18429) and (DSM 18428), *L. brevis* (DSM 18431) and *P. pentosaceus* (DSM 18432)) initially, was used for detoxification of 500 or 1000 ppm of gluten deliberately added to the gluten-free kneads in order to simulate the contamination. After 48 h incubation of the kneads a decrease of about 40% in presence of both gluten concentrations has been observed. Shorter incubation times, i.e. 24 h, displayed similar detoxification percentages, while a 5 h incubation did not allow substantial decreases of gluten concentrations. *L. sanfranciscensis* (DSM 18426) and (DSM 18427) and *L. plantarum* (DSM 18430) in combination displayed an hydrolysis activity of the gluten similar to a pool consisting of higher number of isolates. The same combination of lactic bacteria was suitable to reduce at a threshold of 20 ppm an initial gluten concentration of about 300 ppm, which is a reasonable contamination value for gluten-free starting materials. A similar activity against the gluten can allow higher safety use of gluten-free ingredients involving a gluten biological decontamination during the fermentation process.

(4) Characterisation of Fermented Kneads

In Table 2 the formulations of "natural yeast" based on selected lactic bacteria are reported. Each formulation was used for fermentation of kneads for 12 h at 30° C. A knead fermented only with brewer's yeast for 2 h at 30° C. was used as a control. All the produced kneads after 12 h of fermentation, always reached ΔpH values higher than 2.4 (final pH of the knead about 3.4) (FIG. 3), indicating for all the formulations the ability to provoke a remarkable acidification. In particular, the knead obtained using n. 5 combination (*L. sanfranciscensis* (DSM 18426) and (DSM 18427), and *L. rossiae* (DSM 18429)) displayed highest ΔpH value equal to about 2.6, while n. 3 combination (*P. pentosaceus* (DSM 18432), *L. plantarum* (DSM 18430) and *L. rossiae* (DSM 18428)) displayed the lowest ΔpH value equal to about 2.45. In terms of the maximum acidification velocity ($\mu_{max}$) the kneads obtained using n. 3, 4 (*L. brevis* (DSM 18431), *L. plantarum* (DSM 18430) and *L. rossiae* (DSM 18429)) and 5 combinations displayed highest ΔpH value equal to about 1.3 $h^{-1}$. The acidification power represents one of the parameters to be considered in order to improve the organoleptic characteristics of yeasted product, even if not always the highest acidification power is constantly together with a good bread structure and/or aroma, in particular in the case of the gluten-free flour use. In all the kneads, with the exception of the control knead, the organic acid presence was detected, in particular, the variations were as following: L-lactic acid from 21 to 82 mM, D-lactic acid from 51 to 75 mM and acetic acid from 10 to 30 mM (Table 3 shows concentrations of L- and D-lactic acid, acetic acid and fermentation quotient of kneads fermented for 12 h at 30° C. with formulations of selected lactic bacteria).

TABLE 3

| Knead | L-lactic acid (mM) | D-lactic acid (mM) | Acetic acid ((mM) | Quotient of fermentation [c] |
|---|---|---|---|---|
| 1 | 58.0 | 72.0 | 25.0 | 5.2 |
| 2 | 82.0 | 75.0 | 30.0 | 5.2 |
| 3 | 55.0 | 57.0 | 10.0 | 11.2 |
| 4 | 27.0 | 51.0 | 20.0 | 3.9 |
| 5 | 21.0 | 59.0 | 25.0 | 3.2 |
| Control [a] | nnd [b] | 2.00 | 0.10 | 20 |

[a] Knead fermented at 30° C. for 2 h with brewer's yeast
[b] nd, not determined
[c] Fermentation quotient, molar ratio between lactic acid and acetic acid.

Detected concentrations of three acids and lactic and acetic acid ratio reflect the metabolic profile of the lactic bacteria present in the combination. The organic acid ratio corresponds to that normally found in acid kneads (equal to 4:1), with the exception of the knead obtained with n. 3 combination. The concentration of organic acids, can provide useful information on the contribution that in terms of aroma to the finished product can result from lactic bacteria. Generally, the value of lactic and acetic acid molar ratio, which defines the fermentation quotient, must tend to very low values in order to provide the better contribution. All the produced kneads, with the exception of n. 3 combination, displayed an optimal fermentation quotient. Cell density of produced kneads after 12 h of fermentation is from 9.1 to 9.47 $Log_{10}$ ufc/g of knead. In order to estimate the contribution that the use of natural yeast can give from a nutritional point of view as mineral bioavailability in the bread, the kneads obtained with reported five combinations have been characterised for phytase activity. In Table 4, phytase activity values of the kneads fermented for 12 h at 30° C. with the formulations of selected lactic bacteria are reported, expressed as absorbance at 700 nm.

TABLE 4

| Knead | Phytase activity |
|---|---|
| 1 | 0.008 |
| 2 | 0.053 |
| 3 | 0.040 |
| 4 | 0.061 |
| 5 | 0.048 |
| Control 1 [a] | 0.002 |
| Control 2 [b] | 0.003 |
| Control 3 [c] | 0.002 |

[a] Control 1: knead without bacterial inoculum yeasted for 2 h at 30° C. with 1% brewer's yeast.
[b] Control 2: knead without bacterial inoculum yeasted for 2 h at 30° C. with 0.5% brewer's yeast..
[c] Control 3: knead without bacterial inoculum yeasted for 2 h at 30° C. with 0.25% brewer's yeast..

Figure 4:
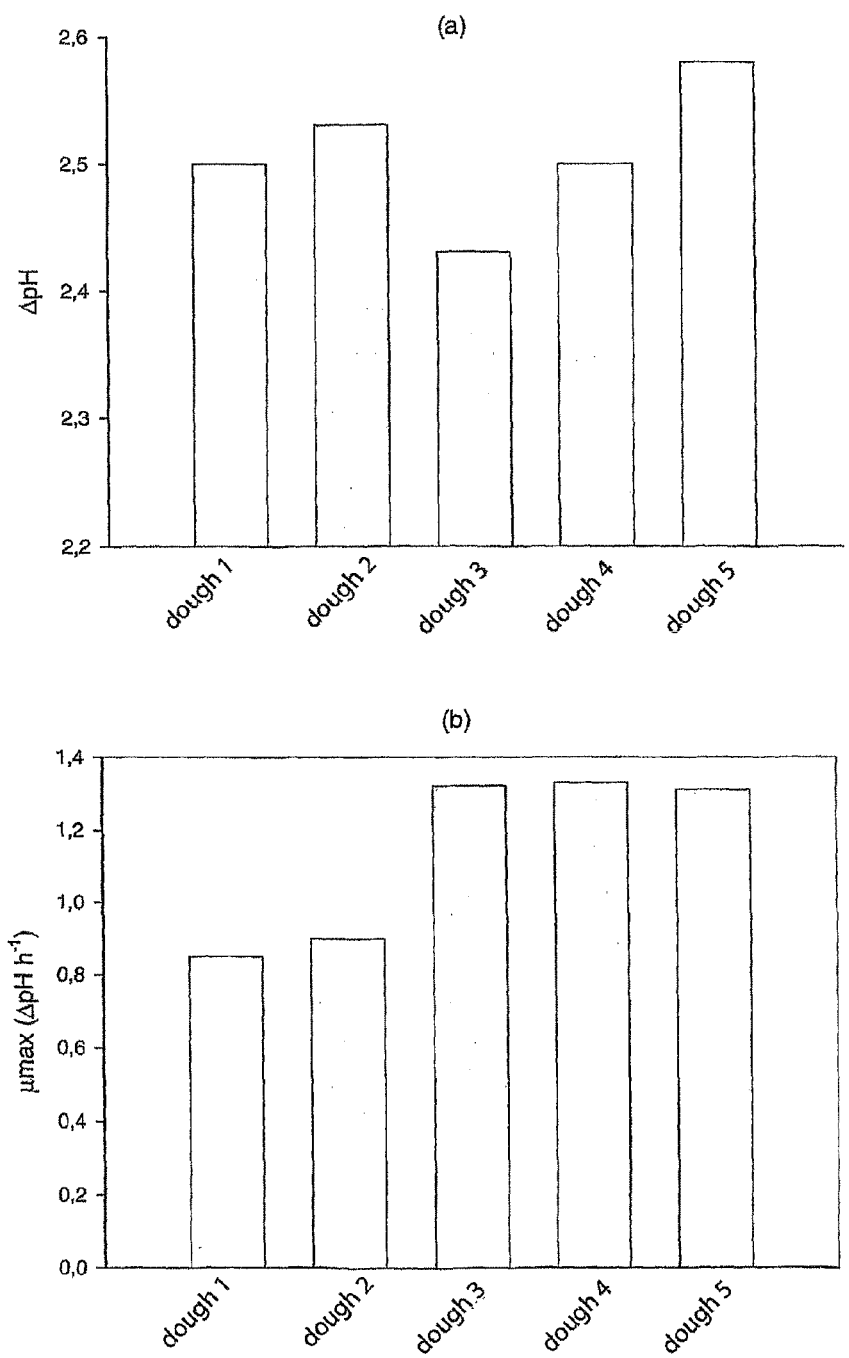
FIG. 4 shows ΔpH (difference between initial and final pH values) (a) and $\mu_{max}$ (highest speed of acidification) (b) of kneads fermented for 12 h at 30° C. with formulations of selected lactic bacteria.
Figure 5:
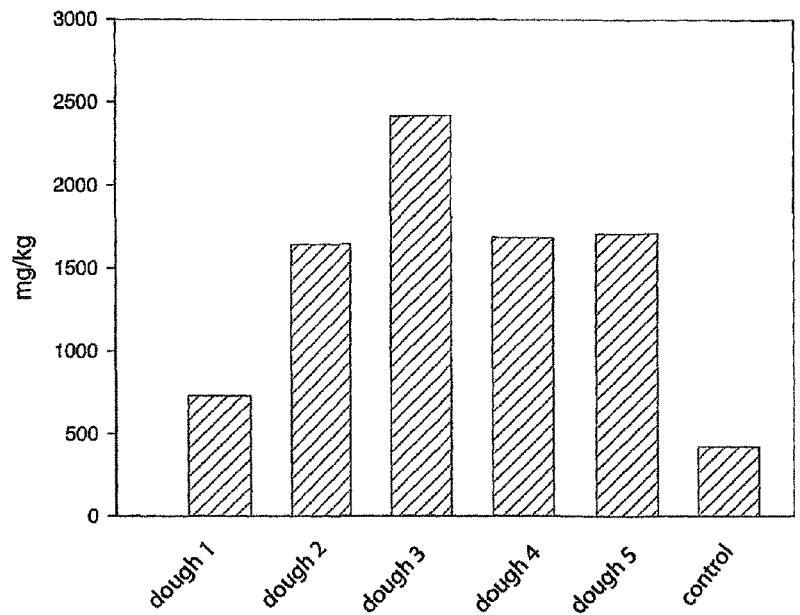
FIG. 5 shows the concentration of total free amino acids of kneads fermented for 12 h at 30° C. with the formulations of selected lactic bacteria.
Figure 6:
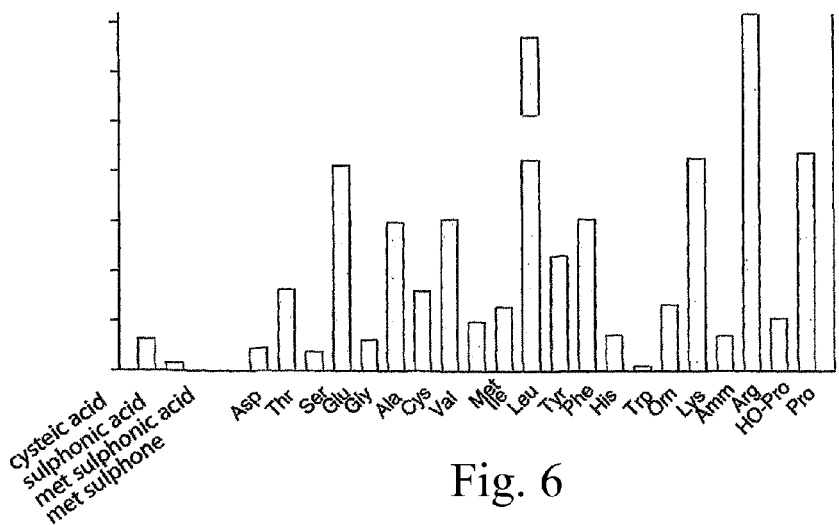
FIG. 6 shows the free amino acid profile as determined by means of Amino Acid Analyser Biochrom 30 of the knead fermented for 12 h at 30° C. with n. 2 formulation of selected lactic bacteria.

With the exception of 1 formulation, all the others (in particular 2 and 4 combinations) displayed phytase activity values approximately 30 times higher than in the control knead. In FIG. 4 total concentration of free amino acids is reported, which for the 5 formulations of "natural yeast" is from 726.54 to 2415.97 mg/kg of knead. The concentration for control knead fermented with brewer's yeast was 420.07 (mg/kg). Fermentation for prolonged time (24 h) with 2 formulation, resulted in doubling the concentration of free amino acids obtained after 12 h of incubation, indicating the possibility to increase the nutritional value and the digestibility of "natural yeast" fermented bread. The amino acid profile of the knead obtained with n. 2 combination, is remarkable for the production of Arg (178.38 mg/kg), Leu (134.09 mg/kg), Glu (82.45 mg/kg) and Pro (87.30 mg/kg) amino acids (FIG. 5).

(5) Production of Gluten-free Bread

Figure 7:
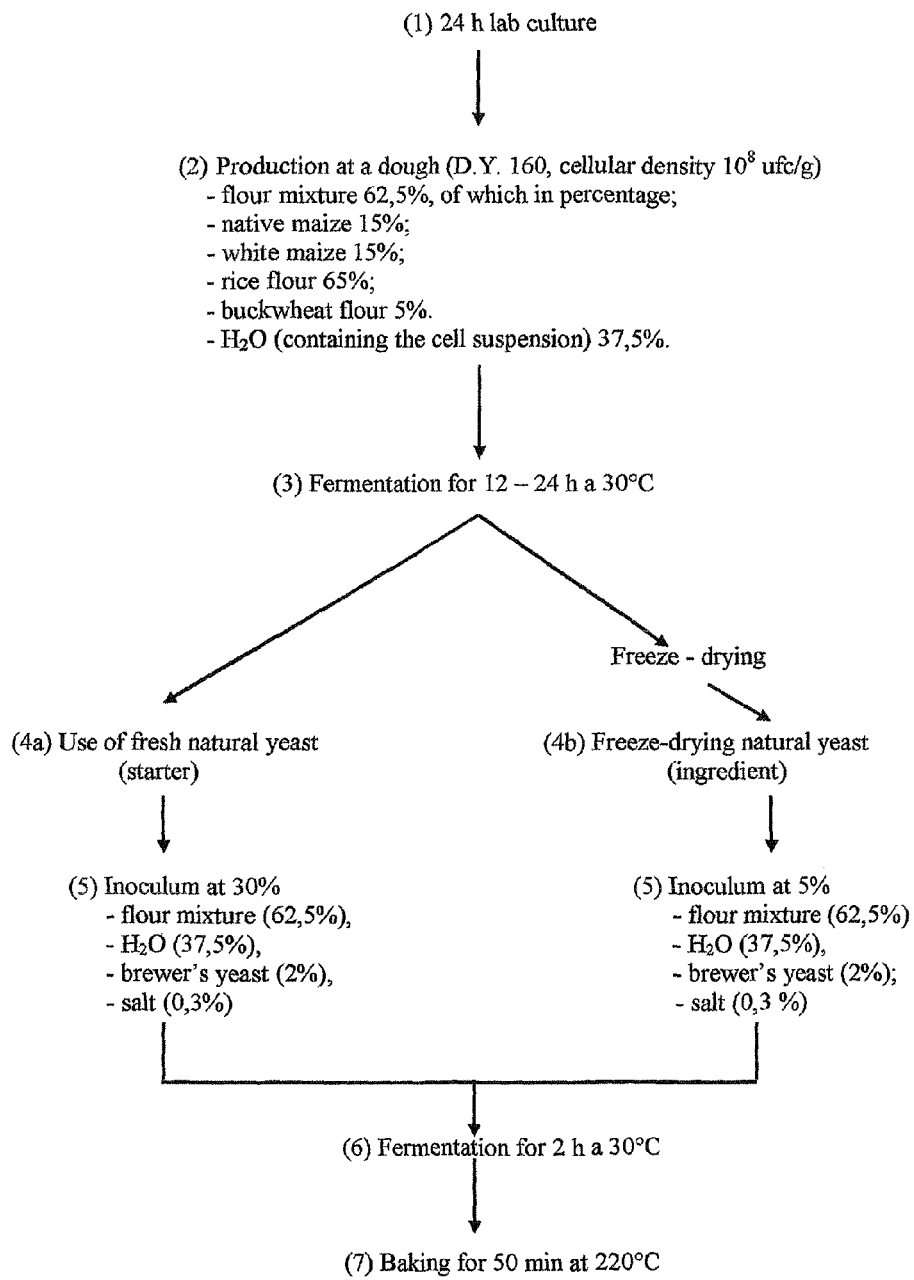
FIG. 7 shows the production protocol of gluten-free bread by means of the use of "natural yeast" based on selected lactic bacteria. In the Figure the reference to the flour mixture in quantitative and qualitative terms is purely indicative and in the second fermentation the addition of other ingredients is considered, as previously specified.
Figure 8:
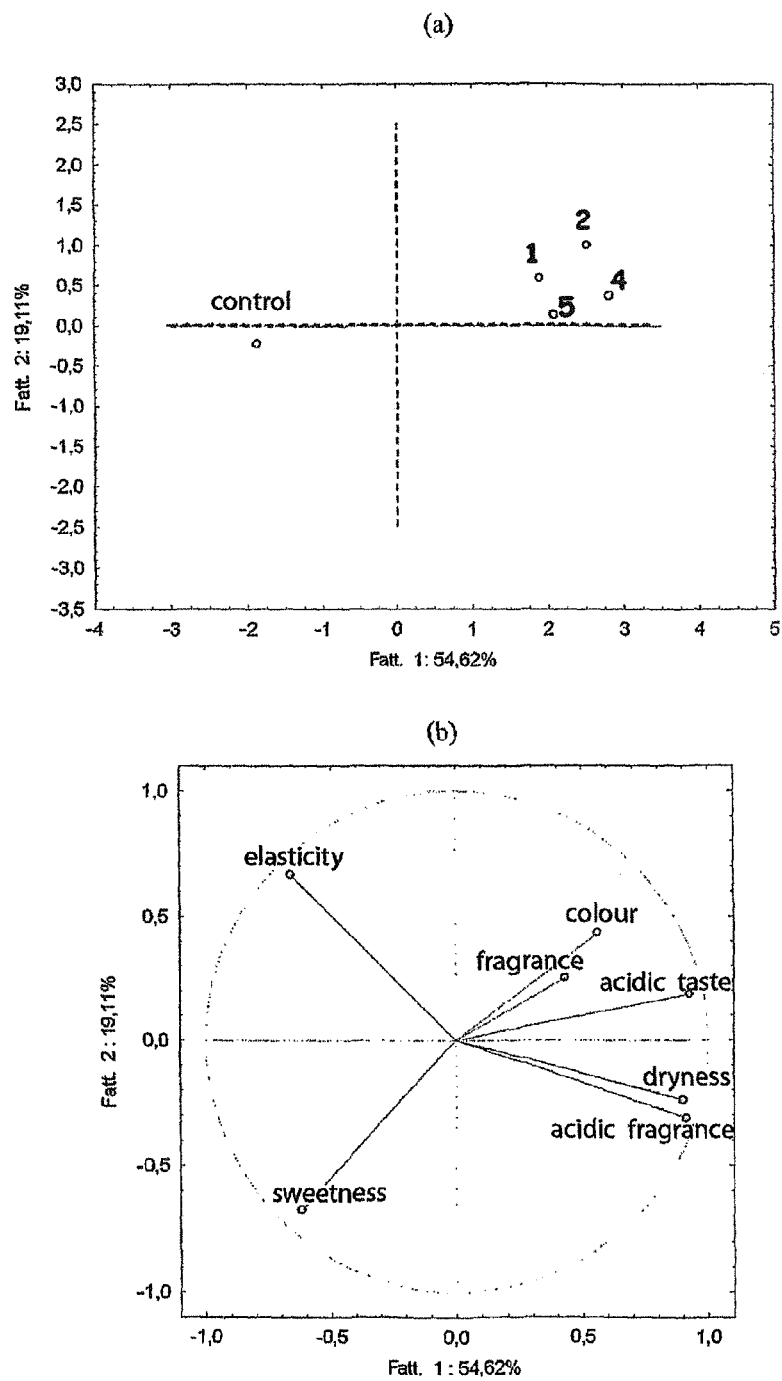
FIG. 8 shows the analysis of major components (PCA) of the data obtained from the sensory analysis of gluten-free breads obtained using fresh "natural yeast" (n. 1, 2, 4 and 5 formulations) in comparison with the brewer's yeast fermented control (C).
Figure 9:
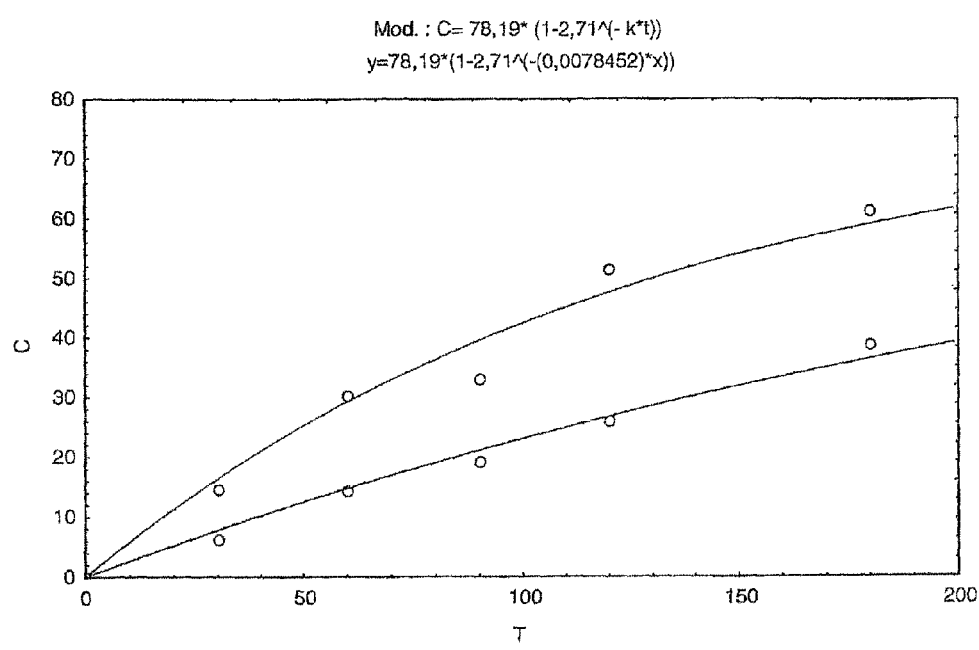
FIG. 9 shows curves concerning the starch hydrolysis index in bread fermented with brewer's yeast (bread control—higher curve) and the natural yeast of the invention (fermented bread—lower curve).

The various formulations of "natural yeast" based on selected lactic bacteria were used for the gluten-free bread production according to biotechnological protocol reported in FIG. 7. The two proposed alternatives correspond to different technological solutions. The use of fresh "natural yeast" as starter for further fermentation process (2 h at 30° C.) represents a traditional technology, not expensive and requiring daily "refresh" of natural yeast". A variant to the use of "natural yeast" as such can be the freezing thereof in order allow a more extended conservation and successive use after reactivation. Drying of "natural yeast" and direct use thereof as ingredient allow easy conservation although not being active in the final fermentation period (2 h at 30° C.). As to the use of brewer's yeast as yeasting agent, the use of 30% fresh "natural yeast" allow an about 10-30 times higher phytase activity to be obtained during fermentation process, resulting in increase of about 21 and 48% of the content of bioavailable $Ca^{2+}$ and $Zn^{2+}$; respectively, and the content of free amino acids is increased by about 10 times. Based on the percentage use of "natural yeast", to be varied according to desired characteristics, above all sensory ones, increments above reported are susceptible to variation. Also the use of frozen "natural yeast", after reactivation, displays same performances of fresh one. All the breads obtained with the different formulations of "natural yeast" based on selected lactic bacteria are characterised by similar or slightly better values of specific volume and hardness in comparison to control bread produced only with brewer's yeast. The produced breads have been subjected to sensory analysis. The sensory parameters evaluated were: elasticity, colour, aroma acid, acid taste, sweetness, dryness and aroma. Every parameter was evaluated according an increasing intensity rating in value range from 0 to 100. For a qualitative evaluation of the sensory profile of each bread, obtained data have been treated by means of statistical analysis of main components (PCA). Two main components reported in FIG. 8 explained 73% of sample total variance. Horizontal axis (Factor 1) indicates the distribution of breed typology, as a function of whole sensory evaluation, vertical axis (Factor 2) expresses bread distribution as a function of each considered sensory parameter. As it apparent from bread distribution on plan defined from the two main components (FIG. 8a), it is deduced that the bread typologies, produced using fresh "natural yeast" displayed quite similar sensory results. From FIG. 8b it is clearly apparent that the sensory typical and appreciated characteristics of aroma, taste and colour are distributed in the plan part wherein breads produced with "natural yeast" are present, confirming the role and contribution of "natural yeast" in terms of aroma and taste. Finally bread produced with 2 formulation, produced on industrial scale, packaged in modified atmosphere (40% $N_2$ and 60% $CO_2$) and subjected to conservation for 6 months. During the entire conservation period microbial contamination phenomena (mildewing and "sticky" bread) without the addition of conservative chemical compounds (e.g., Ca-propionate) were not observed.

The invention claimed is:

1. Mixture comprising:
   isolated lactic bacteria strains for fermentation of gluten-free flours consisting of at least two lactic bacteria strains selected from the group consisting of *Lactobacillus sanfranciscensis* (DSM 18426), *Lactobacillus rossiae* (DSM 18429), *Lactobacillus plantarum* (DSM 18430), *L. sanfranciscensis* (DSM 18427), *Pediococcus pentosaceus* (DSM 18432), *L. rossiae* (DSM 18428) and *Lactobacillus brevis* (DSM 18431); and
   a gluten-free flour.

2. Mixture according to claim 1, wherein the bacteria strains consist of *Lactobacillus sanfranciscensis* (DSM 18426), *Lactobacillus rossiae* (DSM 18429) and *Lactobacillus plantarum* (DSM 18430).

3. Mixture according to claim 1, wherein the bacteria strains consist of *L. sanfranciscensis* (DSM 18426), *L. sanfranciscensis* (DSM 18427) and *L. plantarum* (DSM 18430).

4. Mixture according to claim 1, wherein the bacteria strains consist of *Pediococcus pentosaceus* (DSM 18432), *L. rossiae* (DSM 18428) and *L. plantarum* (DSM 18430).

5. Mixture according to claim 1, wherein the bacteria strains consist of *Lactobacillus brevis* (DSM 18431), *L. rossiae* (DSM 18429) and *L. plantarum* (DSM 18430).

6. Mixture according to claim 1, wherein the bacteria strains consist of *L. sanfranciscensis* (DSM 18426), *L. sanfranciscensis* (DSM 18427) and *L. rossiae* (DSM 18429).

7. Mixture according to claim 1, wherein the cell density of each strain is about $10^8$ cfu/g at the start of fermentation.

8. A gluten-free flour mixture for preparing gluten-free baked products, comprising:
   at least two isolated lactic bacteria strains selected from the group consisting of *Lactobacillus sanfranciscensis* (DSM 18426), *Lactobacillus rossiae* (DSM 18429), *Lactobacillus plantarum* (DSM 18430), *L. sanfranciscensis* (DSM 18427), *Pediococcus pentosaceus* (DSM 18432), *L. rossiae* (DSM 18428) and *Lactobacillus Brevis* (DSM 18431); and
   a gluten-free flour selected from the group consisting of corn, rice, saracen wheat, starch isolated from tapioca, sunflower, linen, teff, sorghum, quinoa, potato, manioca, amaranth, and millet flours.

9. Mixture of gluten-free flours for the preparation of a starter for gluten-free baked products or the same gluten-free baked products, comprising:
   the at least two isolated lactic bacteria strains as defined in claim 1, said mixture of gluten-free flours composition comprising:
   corn starch 10-30%;
   tapioca starch 2-10%;
   rice flour 20-60%; and
   saracen wheat flour 1-10%,
   wherein said percentages are expressed as % weight of total flour composition weight.

10. Mixture according to claim 1, wherein the mixture is gluten-free.

* * * * *

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tacgggaggc agcagtag                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catggtgtga cgggcggt                                                 18

<210> SEQ ID NO 3
<211> LENGTH: 719
<212> TYPE: DNA
<213> ORGANISM: Lactobacillus sanfranciscensis
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (624)..(624)
<223> OTHER INFORMATION: a, c, t, g, unknown or other
<220> FEATURE:
<221> NAME/KEY: modified_base
<222> LOCATION: (634)..(634)
<223> OTHER INFORMATION: a, c, t, g, unknown or other
<220> FEATURE:
<221> NAME/KEY: modified_base
<222> LOCATION: (651)..(651)
<223> OTHER INFORMATION: a, c, t, g, unknown or other
<220> FEATURE:
<221> NAME/KEY: modified_base
<222> LOCATION: (653)..(653)
<223> OTHER INFORMATION: a, c, t, g, unknown or other
<220> FEATURE:
<221> NAME/KEY: modified_base
<222> LOCATION: (674)..(674)
<223> OTHER INFORMATION: a, c, t, g, unknown or other
<220> FEATURE:
<221> NAME/KEY: modified_base
<222> LOCATION: (677)..(677)
<223> OTHER INFORMATION: a, c, t, g, unknown or other
<220> FEATURE:
<221> NAME/KEY: modified_base
<222> LOCATION: (697)..(697)
<223> OTHER INFORMATION: a, c, t, g, unknown or other
<220> FEATURE:
<221> NAME/KEY: modified_base
<222> LOCATION: (699)..(699)
<223> OTHER INFORMATION: a, c, t, g, unknown or other
<220> FEATURE:
<221> NAME/KEY: modified_base
<222> LOCATION: (717)..(717)
<223> OTHER INFORMATION: a, c, t, g, unknown or other

<400> SEQUENCE: 3
agtccccatt gattcttagt gcttgcanta agatgatttt ggatccgact gagtggcgaa   60
ctggtgagta acacgtgggt aacctgccca gaagaagggg ataacacctg gaaacagatg  120

```
ctaataccgt ataacaacaa gaaccacatg gttcttgttt gaaagctggc ctttgtgcta    180
gtgcttctgg atggacccgc ggcgtattag ctagttggtg agataatagc tcaccaaggc    240
aatgatacgt agcagacctg agagggtaat ctgccacaat gggactgaga cacggcccat    300
actcctacgg gaggcagcag tagggaatct tccacaatgg acgaaagtct gatggagcaa    360
cgccgcgtga gtgaagaagg gtttcggctc gtaaaactct gttgttagag aagaacagcc    420
gtgagagcaa ctgctcacgg tatgacggta tctaaccaga aagtcacggc taactacgtg    480
ccagcagccg cggtaatacg taggtggcaa acgttgtccg gatttattgg gcgtaaaggg    540
agcgcaggcg gtttattaag tctgatgtga aagccttcgg cttaacccga aaagtgcatc    600
ggaaactgat aaacttgagt gcanaaaagg atantggaac ttcatgtgta ncngtgaaaa    660
tgcgtaaata tttnaangaa caccagtggc gaaggcngnt atctggtctg taactgnaa     719
```

```
<210> SEQ ID NO 4
<211> LENGTH: 743
<212> TYPE: DNA
<213> ORGANISM: Lactobacillus sanfranciscensis
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (32)..(32)
<223> OTHER INFORMATION: a, c, t, g, unknown or other
<220> FEATURE:
<221> NAME/KEY: modified_base
<222> LOCATION: (552)..(552)
<223> OTHER INFORMATION: a, c, t, g, unknown or other
<220> FEATURE:
<221> NAME/KEY: modified_base
<222> LOCATION: (565)..(565)
<223> OTHER INFORMATION: a, c, t, g, unknown or other
<220> FEATURE:
<221> NAME/KEY: modified_base
<222> LOCATION: (595)..(595)
<223> OTHER INFORMATION: a, c, t, g, unknown or other
<220> FEATURE:
<221> NAME/KEY: modified_base
<222> LOCATION: (598)..(598)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (646)..(646)
<223> OTHER INFORMATION: a, c, t, g, unknown or other
<220> FEATURE:
<221> NAME/KEY: modified_base
<222> LOCATION: (647)..(647)
<223> OTHER INFORMATION: a, c, t, g, unknown or other
<220> FEATURE:
<221> NAME/KEY: modified_base
<222> LOCATION: (675)..(675)
<223> OTHER INFORMATION: a, c, t, g, unknown or other
<220> FEATURE:
<221> NAME/KEY: modified_base
<222> LOCATION: (688)..(688)
<223> OTHER INFORMATION: a, c, t, g, unknown or other
<220> FEATURE:
<221> NAME/KEY: modified_base
<222> LOCATION: (705)..(705)
<223> OTHER INFORMATION: a, c, t, g, unknown or other
<220> FEATURE:
<221> NAME/KEY: modified_base
<222> LOCATION: (712)..(712)
<223> OTHER INFORMATION: a, c, t, g, unknown or other
<220> FEATURE:
```

<221> NAME/KEY: modified_base
<222> LOCATION: (727)..(727)
<223> OTHER INFORMATION: a, c, t, g, unknown or other
<220> FEATURE:
<221> NAME/KEY: modified_base
<222> LOCATION: (734)..(734)
<223> OTHER INFORMATION: a, c, t, g, unknown or other
<220> FEATURE:
<221> NAME/KEY: modified_base
<222> LOCATION: (735)..(735)
<223> OTHER INFORMATION: a, c, t, g, unknown or other
<220> FEATURE:
<221> NAME/KEY: modified_base
<222> LOCATION: (736)..(736)
<223> OTHER INFORMATION: a, c, t, g, unknown or other
<220> FEATURE:
<221> NAME/KEY: modified_base
<222> LOCATION: (738)..(738)
<223> OTHER INFORMATION: a, c, t, g, unknown or other

<400> SEQUENCE: 4

```
gacgantccc cattgattct tagtgcttgc antaagatga ttttggatcc gactgagtgg      60
cgaactggtg agtaacacgt gggtaacctg cccagaagaa ggggataaca cctgaaaaca     120
gatgctaata ccgtataaca acaagaacca catggttctt gtttgaaagc tggcctttgt    180
gctagtgctt ctggatggac ccgcggcgta ttagctagtt ggtgagataa tagctcacca     240
aggcaatgat acgtagcaga cctgagaggg taatctgcca caatgggact gagacacggc     300
ccatactcct acgggaggca gcagtaggga atcttccaca atggacgaaa gtctgatgga     360
gcaacgccgc gtgagtgaag aagggtttcg gctcgtaaaa ctctgttgtt agagaagaac     420
agccgtgaga gcaactgctc acggtatgac ggtatctaac cagaaagtca cggctaacta     480
cgtgccagca gccgcggtaa tacgtaggtg gcaaacgttg tccggattta ttgggcgtaa     540
aagggagcgc angcggttta ttaantctga tgtgaaagcc ttcgcttaac ccganaantg     600
catcgaaact gataaacttg aatgcaaaaa gggggggggg ggggnnntgt gtaccgttaa     660
attcctaaat atttnaaagg aacaccantg gcgaaggcgg ctatntggtc tntaaaaaaa     720
aaacacnccc cctnnntncg ggg                                            743
```

<210> SEQ ID NO 5
<211> LENGTH: 749
<212> TYPE: DNA
<213> ORGANISM: Lactobacillus plantarum

<400> SEQUENCE: 5

```
tttcttccca atggacgaaa gtctgatgga gcaacgccgc gtgagtgaag aagggtttcg      60
gctcgtaaaa ctctgttgtt aaagaagaac atatctgaga gtaactgttc aggtattgac    120
ggtatttaac cagaaagcca cggctaacta cgtgccagca gccgcggtaa tacgtaggtg     180
gcaagcgttg tccggattta ttgggcgtaa agcgagcgca ggcggttttt taagtctgat     240
gtgaaagcct tcggctcaac cgaagaagtg catcggaaac tgggaaactt gagtgcagaa     300
gaggacagtg gaactccatg tgtagcggtg aaatgcgtag atatatggaa gaacaccagt     360
ggcgaaggcg gctgtctggt ctgtaactga cgctgaggct cgaaagtatg ggtagcaaac     420
aggattagat accctggtag tccataccgt aaacgatgaa tgctaagtgt tgagggtttt     480 ccgccctica gtgctgcagc taacgcatta agcattccgc ctggggagta cggccgcaag     540
```

-continued

```
gctgaaactc aaaggaattg acgggggccc gcacaagcgg tggagcatgt ggtttaattc      600
gaagctacgc gaagaacctt accaggtctt gacatactat gcaaatctaa gagattagac      660 gttcccttc  ggggacatgg atacaggtgg tgcatggttg tcgtcagctc gtgtcgtgag      720
atgttgggtt aagtcccgca acgagcgca                                         749
```